(12) United States Patent
Khanna et al.

(10) Patent No.: US 10,631,931 B2
(45) Date of Patent: *Apr. 28, 2020

(54) LIQUID LIGHT GUIDE CATHETER HAVING BIOCOMPATIBLE LIQUID LIGHT GUIDE MEDIUM

(71) Applicant: The Spectranetics Corporation, Colorado Springs, CO (US)

(72) Inventors: Krishn Khanna, Colorado Springs', CO (US); Robert Splinter, Colorado Springs, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 235 days.

This patent is subject to a terminal disclaimer.

(21) Appl. No.: 15/372,141

(22) Filed: Dec. 7, 2016

(65) Prior Publication Data

US 2017/0086924 A1 Mar. 30, 2017

Related U.S. Application Data

(63) Continuation of application No. 11/923,488, filed on Oct. 24, 2007, now Pat. No. 9,848,952.

(51) Int. Cl.
*A61B 18/24* (2006.01)
*G02B 6/032* (2006.01)
(Continued)

(52) U.S. Cl.
CPC ............. *A61B 18/24* (2013.01); *A61B 18/20* (2013.01); *A61B 18/245* (2013.01); *A61L 29/02* (2013.01);
(Continued)

(58) Field of Classification Search
None
See application file for complete search history.

(56) References Cited

U.S. PATENT DOCUMENTS 3,995,934 A 12/1976 Nath
4,045,119 A 8/1977 Eastgate
(Continued)

OTHER PUBLICATIONS

"Lactated Ringer's Solution," from Wikipedia website, http://en.wikipedia.org/wiki/Lactated_Ringer%27ssolution, printed Sep. 6, 2007, 2 pages, no date.
(Continued)

*Primary Examiner* — Carl H Layno
*Assistant Examiner* — Manolis Pahakis

(57) ABSTRACT

A method of delivering light energy to target matter in a mammalian body is described. The method may include inserting at least a portion of a catheter into a patient's vasculature, wherein the catheter comprises an open distal tip, a lumen extending proximally from the open distal tip, and at least one optical fiber within the lumen, wherein the at least one optical fiber has a distal end. The method may include flowing a liquid light guide medium through the open-ended catheter tip, wherein the liquid light guide medium flows beyond the distal end of the at least one optical fiber, wherein the liquid light guide medium comprises a magnesium chloride solution having an ion concentration that is isotonic with blood and tissue. The method may include forming a fluid optical channel with the liquid light guide medium between the catheter and the target matter. Other methods are described.

8 Claims, 9 Drawing Sheets

(51) Int. Cl.
  *A61B 18/20* (2006.01)
  *A61L 29/02* (2006.01)
  *A61B 18/22* (2006.01)
  *A61B 18/00* (2006.01)

(52) U.S. Cl.
  CPC .... *G02B 6/032* (2013.01); *A61B 2018/00577* (2013.01); *A61B 2018/206* (2013.01); *A61B 2018/2222* (2013.01); *A61B 2018/2244* (2013.01); *A61B 2018/2261* (2013.01)

(56) References Cited

U.S. PATENT DOCUMENTS

| | | |
|---|---|---|
| 4,053,845 A | 10/1977 | Gould |
| 4,217,904 A | 8/1980 | Zahorsky |
| 4,448,188 A | 5/1984 | Loeb |
| 4,620,979 A | 11/1986 | Schachar |
| 4,641,912 A | 2/1987 | Goldenberg |
| 4,686,979 A | 8/1987 | Gruen et al. |
| 4,732,448 A | 3/1988 | Goldenberg |
| 4,735,606 A | 4/1988 | Davison |
| 4,747,405 A | 5/1988 | Leckrone |
| 4,748,982 A | 6/1988 | Horzewski et al. |
| 4,772,268 A | 9/1988 | Bates |
| 4,784,132 A | 11/1988 | Fox et al. |
| 4,794,931 A | 1/1989 | Yock |
| 4,799,754 A | 1/1989 | Goldenberg |
| 4,807,620 A | 2/1989 | Strul et al. |
| 4,830,460 A | 5/1989 | Goldenberg |
| 4,834,093 A | 5/1989 | Littleford et al. |
| 4,842,582 A | 6/1989 | Mahurkar |
| 4,844,062 A | 7/1989 | Wells |
| 4,848,336 A | 7/1989 | Fox et al. |
| 4,899,363 A | 2/1990 | Murray et al. |
| 4,919,508 A | 4/1990 | Grace et al. |
| 4,924,863 A | 5/1990 | Sterzer |
| 4,960,108 A | 10/1990 | Reichel et al. |
| 4,961,809 A | 10/1990 | Martin |
| 4,998,794 A | 3/1991 | Holzman |
| 5,016,964 A | 5/1991 | Donnelly |
| 5,024,234 A | 6/1991 | Leary et al. |
| 5,041,108 A | 8/1991 | Fox et al. |
| 5,054,492 A | 10/1991 | Scribner et al. |
| 5,054,500 A | 10/1991 | Littleford et al. |
| 5,057,073 A | 10/1991 | Martin |
| 5,157,750 A | 10/1992 | Grace et al. |
| 5,165,773 A | 11/1992 | Nath |
| 5,179,961 A | 1/1993 | Littleford et al. |
| 5,188,632 A | 2/1993 | Goldenberg |
| 5,203,338 A | 4/1993 | Jang |
| 5,250,045 A | 10/1993 | Bohley |
| 5,263,952 A | 11/1993 | Grace et al. |
| 5,263,953 A | 11/1993 | Bagby |
| 5,267,341 A | 11/1993 | Shearin |
| 5,267,993 A | 12/1993 | Grace et al. |
| 5,304,171 A | 4/1994 | Gregory et al. |
| 5,315,614 A | 5/1994 | Grace et al. |
| 5,321,783 A | 6/1994 | Nielson et al. |
| 5,339,441 A | 8/1994 | Kardos et al. |
| 5,350,375 A | 9/1994 | Deckelbaum et al. |
| 5,352,197 A | 10/1994 | Hammersmark et al. |
| 5,383,199 A | 1/1995 | Laudenslager et al. |
| 5,400,428 A | 3/1995 | Grace |
| 5,412,682 A | 5/1995 | Laudenslager et al. |
| 5,412,750 A | 5/1995 | Nath |
| 5,415,653 A | 5/1995 | Wardle et al. |
| 5,429,604 A | 7/1995 | Hammersmark et al. |
| 5,429,617 A | 7/1995 | Hammersmark et al. |
| 5,438,587 A | 8/1995 | Kinley |
| 5,440,664 A | 8/1995 | Harrington et al. |
| 5,456,680 A | 10/1995 | Taylor et al. |
| 5,470,330 A | 11/1995 | Goldenberg et al. |
| 5,484,433 A | 1/1996 | Taylor et al. |
| 5,514,128 A | 5/1996 | Hillsman et al. |
| 5,571,151 A | 11/1996 | Gregory |
| 5,573,531 A | 11/1996 | Gregory |
| 5,623,940 A | 4/1997 | Daikuzono |
| 5,643,251 A | 7/1997 | Hillsman et al. |
| 5,649,923 A | 7/1997 | Gregory et al. |
| 5,722,972 A | 3/1998 | Power et al. |
| 5,737,473 A | 4/1998 | Nath |
| 5,817,144 A | 10/1998 | Gregory |
| 5,824,026 A | 10/1998 | Diaz |
| 5,836,940 A | 11/1998 | Gregory |
| 5,836,946 A | 11/1998 | Diaz et al. |
| 5,859,946 A | 1/1999 | Wojcik et al. |
| 5,860,948 A | 1/1999 | Buscemi |
| RE36,104 E | 2/1999 | Solar |
| 5,976,124 A | 11/1999 | Reiser |
| 5,989,243 A | 11/1999 | Goldenberg |
| 6,066,130 A | 5/2000 | Gregory et al. |
| 6,117,128 A | 9/2000 | Gregory |
| 6,163,641 A | 12/2000 | Eastgate |
| 6,166,806 A | 12/2000 | Tjin |
| 6,290,668 B1 | 9/2001 | Gregory et al. |
| 6,314,226 B1 | 11/2001 | Nath |
| 6,418,257 B1 | 7/2002 | Nath |
| 6,458,098 B1 | 10/2002 | Kanesaka |
| 6,743,208 B1 | 6/2004 | Coyle |
| 7,050,692 B2 | 5/2006 | Harlan et al. |
| 2001/0027316 A1 | 10/2001 | Gregory |
| 2002/0049402 A1 | 4/2002 | Peacock, III et al. |
| 2003/0104073 A1 | 6/2003 | Johansson et al. |
| 2004/0082022 A1 | 4/2004 | Segall et al. |
| 2006/0241648 A1 | 10/2006 | Bleich et al. |
| 2007/0021713 A1 | 1/2007 | Kumar et al. |
| 2009/0210039 A1 | 8/2009 | Boyden et al. |
| 2009/0254074 A1 | 10/2009 | Splinter et al. |

OTHER PUBLICATIONS

Concise Dictionary of Modern Medicine, Definition of Ringer's lactate solution, 2002 by The McGraw-Hill Companies, Inc.

Gregory, Kenton W. and Anderson R. Rox, "Light Core Light Guide for Laser Angioplasty," IEE Journal of Quantum Electronics, vol. 26, No. 12 (Dec. 1990), pp. 2289-2296.

Grundfest, Warren S., MD, et al., "Laser Ablation of Human Atherosclerotic Plaque Without Adjacent Tissue Injury," JACC vol. 5, No. 4, (Apr. 1985), pp. 929-933.

Hofmann, R. et al., Laser-Induced Shock Wave Ureteral Lithotripsy Using Q-Switched Nd:YAG Laser, Journal of Endourology, vol. 2, No. 2, 1990, pp. 169-174.

Lactated Ringer's Solution, Baxter Healthcare Corporation, 2003.

LIQUID LIGHT GUIDE CATHETER HAVING BIOCOMPATIBLE LIQUID LIGHT GUIDE MEDIUM

CROSS-REFERENCES TO RELATED APPLICATIONS

The present application is a continuation of U.S. application Ser. No. 11/923,488, filed Oct. 24, 2017, which issued as U.S. Pat. No. 9,848,952, entitled LIQUID LIGHT GUIDE CATHETER HAVING BIOCOMPATIBLE LIQUID LIGHT GUIDE MEDIUM, which is hereby incorporated by reference in its entirety for all purposes.

STATEMENT AS TO RIGHTS TO INVENTIONS MADE UNDER FEDERALLY SPONSORED RESEARCH OR DEVELOPMENT

NOT APPLICABLE

BACKGROUND OF THE INVENTION

Vascular occlusions restrict the flow of blood to tissue and organs and can cause a variety of problems. For example, occlusions that restrict blood flow to the heart can cause heart attacks and angina, and occlusions that restrict blood flow in cerebral blood vessels (e.g., cerebral arteries and veins) can cause strokes and other neurological problems. It is therefore desirable that these occlusions be opened up and removed.

One approach to treating occlusions is to apply drugs that cause the vessel to dilate. However, these drugs are not suitable for all patients, and even when they are suitable their ability to slow and reverse the occluding process is usually only temporary. Drugs may also be administered that dissolve occlusions. However, these drugs can cause serious side-effects, such as hemorrhaging, and do not dissolve many types of vascular occlusions.

Another approach to treating occlusions is angioplasty, where a device (typically a catheter) for dilating an occluded vessel is introduced through an opening in the skin and wall of a large vessel, such as the brachial or femoral artery. When the device reaches the site of the occlusion, treatment is administered to break up or otherwise treat the occlusion. For example, in balloon angioplasty a guide wire first reaches the site of the occlusion and guides a catheter lumen to the site. The catheter lumen has an inflatable balloon near its tip that inflates to compact the occlusion and stretch the walls of the vessel. Unfortunately, the results of balloon angioplasty can also be temporary as the occluding process may continue and re-block the vessel.

Additional approaches to treating occlusions include recanalizing the occlusion by cutting and/or pulverizing the occlusion with a vascular catheter. Here also guide wires may first reach the occlusion site and guide a catheter lumen to the occlusion. The guide wire tips are designed to be relatively small and stiff so that they can more easily penetrate and advance through the occlusion, providing a path or rail for the subsequently advancing catheter to follow through the occlusion. When the catheter reaches the occlusion, a device at the catheter's distal tip is advanced into the occlusion where it performs the operation to cross or penetrate the occlusion. The catheter may also include components that capture, suction or otherwise prevent the occlusion fragments from traveling downstream and creating another blockage. These approaches are relatively effective for treating acute occlusions made of relatively soft tissue and occlusions that do not completely block the passage of blood and other fluids through the vessel, but are less effective for treating calcified, fibrotic occlusions that are difficult to penetrate with conventional guide wires.

Vascular occlusions may also be treated by ablation with light energy (e.g., laser atherectomy). These approaches involve positioning optical fibers at the site of the occlusion and delivering light energy through the fibers to ablate the occlusion. The optical fibers are typically made of fused silica or quartz, and are fairly inflexible unless they are made very thin. Unfortunately, thin optical fibers can only deliver small amounts of light energy to the occlusion site. Also, the thin delicate fibers are easily damaged during ablation of hard occlusion materials like calcified deposits. Moreover, the light energy is attenuated over a relatively short distance as it passes through a small optical fiber. Thus, there is a need for new approaches to deliver light energy to a vascular occlusion.

BRIEF SUMMARY OF THE INVENTION

Embodiments of the invention include a catheter system to ablate target matter within a mammalian body using light energy. The system may include an open-ended catheter tip through which a liquid light guide medium flows to the target matter, where at least a portion of the liquid light guide medium exiting the catheter tip creates a fluid optical channel to transmit the light energy from the catheter tip to the target matter. The system may also include a catheter lumen whose distal end comprises the open-ended catheter tip, where the lumen contains a distal end of at least one optical fiber that transmits the light energy to the liquid light guide medium, and where the lumen acts as a conduit for the liquid light guide medium flowing through the catheter tip. The system may still further include a light source to generate the light energy, where the light source is optically coupled to at least one optical fiber, and a liquid light guide medium source fluidly coupled to the catheter lumen, where the medium source comprises a reservoir of the liquid light guide medium comprising a magnesium chloride solution or a lactated Ringer's solution.

Embodiments of the invention also include a catheter system for delivering laser light energy to target matter in a mammalian body. The system may include an open-ended catheter tip through which a liquid light guide medium flows to the target matter, where at least a portion of the liquid light guide medium exiting the catheter tip creates a fluid optical channel to transmit the laser light energy from the catheter tip to the target matter. The system may also include a lumen having a distal end coupled to the open-ended catheter tip, and a branched connector comprising first and second branch inlets and an outlet coupled to a proximal end of the lumen. One or more optical fibers may pass through the first branch of the connecter and into the lumen, where the optical fibers are optically coupled to a laser that generates the laser light energy. A liquid light guide medium source may be coupled to the second branch of the connector, where the medium source comprises a reservoir of the liquid light guide medium comprising a magnesium chloride solution or a lactated Ringer's solution.

Embodiments of the invention still further include a catheter system to deliver light energy to target matter in a mammalian body. The system may include an open-ended catheter tip through which it liquid light guide medium flows to the target matter, where at least is portion of the liquid light guide medium exiting the catheter tip creates a fluid optical channel to transmit the light energy from the catheter tip to the target matter. The system may also include a catheter lumen whose distal end comprises the open-ended catheter tip, where the lumen acts as a conduit for the light energy transmitted though the liquid light guide medium in the conduit. The system may further include a light source to generate the light energy, where the light energy is transmitted from the source to the open-ended catheter tip exclusively through the liquid light guide medium in the catheter lumen, and a liquid light guide medium source fluidly coupled to the catheter lumen.

Embodiments of the invention also further include methods of delivering light energy to target matter in it mammalian body. The methods may include the steps of positioning an open-ended catheter tip proximate to the target matter, and flowing a liquid light guide medium comprising a magnesium chloride solution or a lactated Ringer's solution through the open-ended catheter tip towards the target matter, where at least a portion of the liquid light guide medium exiting the catheter tip creates a fluid optical channel to transmit the light energy from the catheter tip to the target matter. The methods may further include activating a light source to generate the light energy that is transmitted through the fluid optical channel to the target matter.

Embodiments of the invention still also include a catheter system that includes a catheter to define a catheter lumen which acts as a conduit for a liquid light guide medium. The catheter has an open-ended distal end through which the liquid light guide medium flows to the target matter. At least a portion of the liquid light guide medium exiting the catheter tip creates a fluid optical channel to transmit the light energy from the catheter tip to the target matter. The system may also include an optical fiber extending into the catheter lumen and having a distal end terminating inside the catheter. The optical fiber transmits the light energy to the liquid light guide medium. The system may further include a liquid light guide medium source fluidly coupled to the catheter lumen. The medium source includes a reservoir of the liquid light guide medium, which may be a magnesium chloride solution or a lactated Ringer's solution.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral and follows a hyphen to denote one of multiple similar components. When reference is made to a reference numeral without specification to an existing sublabel, it is intended to refer to all such multiple similar components.

DETAILED DESCRIPTION OF THE INVENTION

Catheter systems are described that use a liquid-phase light guide to transmit light energy to target matter (e.g., an occlusion) inside a mammalian body (e.g., an occlusion site inside the vasculature of a human patient). The catheter systems have an open-ended catheter tip that directs a liquid light guide medium from the end of the catheter to the target matter. The flow of light guide medium out of the catheter tip creates an optical fluid channel between the medium and the surrounding blood. The difference in the indices' of refraction between the medium and the blood are large enough to facilitate total internal reflection of the light energy transmitted from the catheter tip to the target medium.

The liquid light guide medium is a biocompatible fluid that has excellent light energy transmission characteristics at the light wavelengths used. For example, a light source that is particularly capable of ablating calcified, fibrotic occlusions is the XeCl Excimer laser, which transmits laser light energy around the 308 nm wavelength. It has been discovered that solutions of magnesium chloride and lactated Ringer's solution are very effective for liquid light transmission at this wavelength. Moreover, these solutions have excellent biocompatibility when they are introduced into as patient. For example, the ion concentrations of these solutions may be set to achieve an isotonic state with blood and tissue. This helps avoid hemolysis, which can be caused when hypotonic pure water substitutes for the isotonic solutions.

Magnesium chloride and lactated Ringer's solutions are also less toxic than other salts that may be used as liquid light guide mediums. For example, solutions of calcium chloride ($CaCl_2$) are normally more concentrated than a comparable magnesium chloride solution with an index of retraction between about 1.37 and 1.42. Calcium chloride solutions at these concentrations are less biocompatible, and may cause necrosis if introduced to a patient's muscle tissue. However, magnesium chloride solutions are biocompatible at the concentration needed to achieve a similar index of refraction.

Exemplary Catheter Systems

Figure 1:
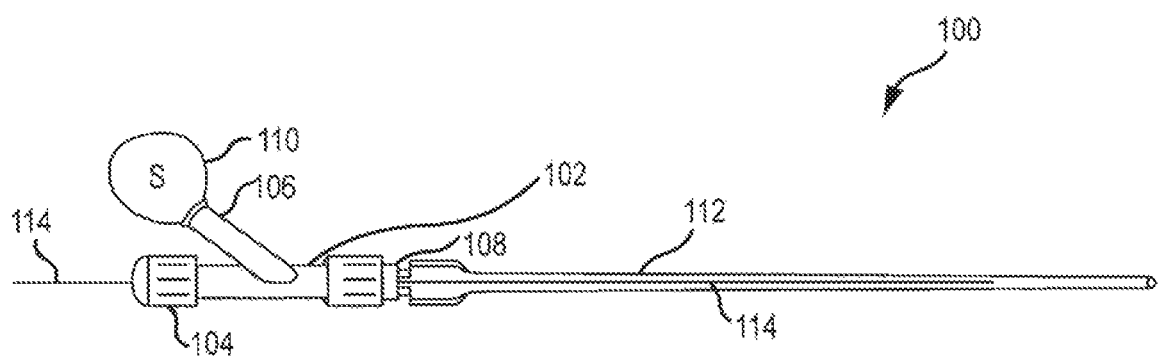
FIG. 1 shows an embodiment of a liquid-light guide catheter assembly according to embodiments of the invention.

FIG. 1 shows an embodiment of a liquid-light guide catheter assembly 100 according to embodiments of the invention. The catheter assembly 100 includes a Y-connector 102 having branched proximal ends 104 and 106 that merge into a single distal end 108. One proximal end is coupled to a light source (not shown) which generates light energy that is transmitted through the catheter assembly to the target matter. The other proximal end is fluidly coupled to a source 110 for the liquid light guide medium that transmits the light energy and forms a fluid optical channel for transmitting the light energy from the end of the assembly 100 to the target matter.

The distal end 108 of the Y-connector 102 is coupled to a proximal end of a catheter lumen 112. The distal end of the lumen 112 is open ended so the liquid light guide medium can exit the catheter assembly 100 and form the fluid optical channel between the assembly and target matter. The lumen 112 may also provide a path for an guidewire (not shown) to direct the distal end of the lumen to a position proximate to the target matter. The lumen interior may also accommodate an optical fiber 114 that transmits light energy from the light source to a distal end of the fiber. The fiber's distal end may terminate inside the lumen 112 where light energy exits the fiber 114 and is transmitted through the liquid light guide medium to the distal end of the lumen and then through the fluid optical channel to the target matter.

The catheter tubing may be made from flexible, biocompatible materials with refractive indices that facilitate total internal reflection at the wavelengths of light energy used. For example, the tubing may be made from a material with an index of refraction that is lower than the liquid light guide medium flowing through the lumen. Examples of materials that fulfill these criteria at the 30 nm wavelength include fluoropolymers (e.g., fluorinated ethylene propylene (FEP) or polytetrafluoroethylene (PTFE) material) with refractive indices below that of water, such as Teflon® AF2400™ and Teflon® FEP from DuPont.

The liquid light guide medium may be selected for its efficient transmission of the light energy at the wavelengths generated by the light source. For example, embodiments of the present invention include an Excimer laser using a xenon chloride (XeCl) lasing medium as the light source. A XeCl Excimer laser generates laser light energy with a wavelength of about 308 nm, so a liquid light guide medium is selected for efficient transmission around this wavelength. The liquid mediums with excellent transmittance at this wavelength include aqueous magnesium chloride solutions, such as solutions of pure magnesium chloride, solutions of anhydrous magnesium chloride, and solutions of hydrated magnesium chloride (e.g., magnesium chloride hexahydrate). They also include Lactated Ringer's solution, which may include aqueous ions of sodium, chloride, potassium, calcium and lactate. The sources of these ions in a lactated Ringer's solution may come from sodium chloride (NaCl), sodium lactate (NaC$_3$H$_5$O$_3$), calcium chloride (CaCl$_2$), and potassium chloride (KCl), though as will be appreciated by one of skill in the art, other combinations of salts may be used. As noted above, both magnesium chloride and lactated Ringer's solution have excellent biocompatibility (e.g., low toxicity) as well as excellent light transmission characteristics at the 308 nm wavelength.

Figure 2:
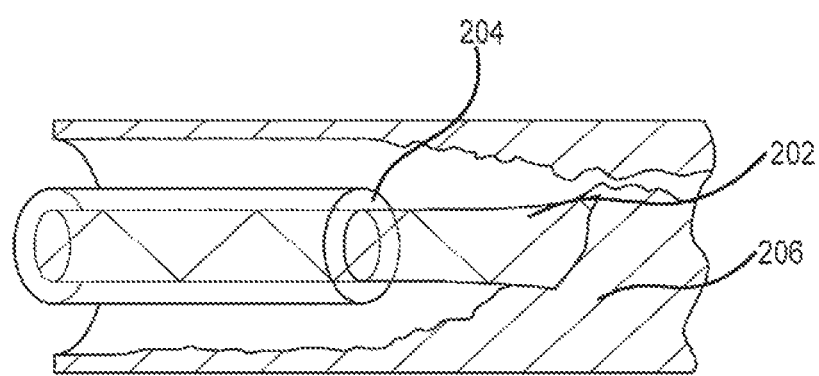
FIG. 2 shows a schematic of a fluid optical channel formed between an open-ended catheter tip and a vascular occlusion according to embodiments of the invention.

FIG. 2 shows how the liquid light guide medium flowing from the distal end of catheter lumen forms a temporary fluid optical channel 202 between the catheter tip 204 and a vascular occlusion 206. In this illustration, the tip of the catheter lumen 204 is positioned adjacent to the vascular occlusion 206 that represents the target matter. The liquid light guide medium is then pumped out the distal catheter tip 204 to establish the fluid optical channel 202. The liquid light guide medium may be supplied from a source (not shown) that is fluidly connected to a proximal end of the catheter lumen and pumped through the length of the lumen.

When the fluid flow reaches the vascular occlusion 206 and establishes the fluid optical channel 202, a light source (not shown) may be activated to transmit light energy through the medium in the catheter and the channel 202 into the occlusion 206. When the light source is a XeCl Excimer laser, the light energy may be a high energy pulse of 308 nm laser light that can ablate material from the occlusion 206.

The liquid light guide medium is selected to create total internal reflection of the light energy transmitted through the fluid optical channel 202. Total internal reflection may be established when the angle of incidence of the light transmitted through the lumen of the tubing has an angle with the normal surface of the tubing (or blood surrounding the fluid optical channel) satisfies the condition for total internal reflection defined by the fact that the angle of incidence is greater than a critical angle d established by the ratio of the index of refraction of the medium ($n_1$) and the surrounding blood ($n_2$) as follows:

$$\sin d = \frac{n_2}{n_1}$$

Thus, increasing the difference in the index of refraction between the cure and surrounding blood increases the angle at which off-axis rays can be conducted in the core and minimizes losses arising from bends in tortuous arteries. In addition, the medium should not have significant optical absorption or scattering at the wavelength of the light energy.

Biocompatible concentrations of magnesium chloride and lactated Ringer's solutions have indices of refraction (n) in the range of about 1.33 to about 1.42 for 308 nm light energy. These refractive indices can be made different enough from the refractive index of blood (where n is typically about 1.34-1.36) to establish as high level of internal reflection for the 308 nm light energy transmitted through the fluid optical channel. In effect, the blood will act as the cladding material for the fluid optical channel established by the flowing optical light guide medium.

When the light ablation forms an indentation or cavity in the target matter, the remaining matter (i.e., tissue) can form a cladding surface for the fluid optical channel. Like blood, bodily tissue normally has a lower index of refraction than the liquid light guide medium and may facilitate total internal reflection of the light energy traveling in the fluid optical channel. Thus, ablating the target material may progress from a fluid optical channel formed from a liquid light guide medium core surrounded by blood, to a channel formed by the liquid light guide medium flowing into an opening or cavity formed in the ablated target material. This may allow the efficient transmission of the light energy deep into a vascular occlusion.

Figure 3:
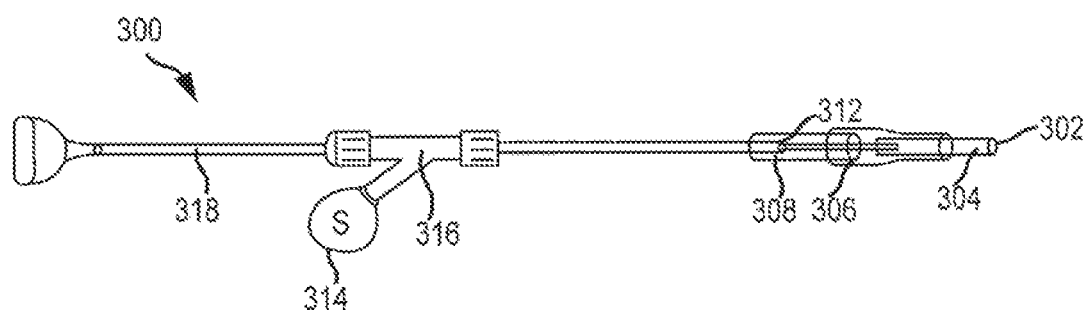
FIG. 3 show a schematic of a catheter system with a segmented distal portion according to embodiments of the invention.

Referring now to FIG. 3, a schematic of another catheter system 300 with a segmented distal portion according to embodiments of the invention is shown. The distal part a this system includes an open-ended distal tip 302 made from a tubing segment 304 that is coupled at its proximal end to a piece of shrink tubing 306 that connects the tubing segment 304 to a second piece of shrink tubing 308, which in turn is coupled at the opposite end to the distal and of catheter lumen 312. Tubing segment 304 may have an outer diameter that is smaller than the inner diameter of shrink tubing 306, so it can be inserted into the shrink tubing. For example, the first segment may be about 1 cm long piece of tubing with an inner diameter greater than about 0.7 mm. Tubing segment 304 and shrink tubing pieces 306, 308 together form a conduit for a liquid light guide medium and optical fiber 309.

The catheter lumen 312 provides a fluid conduit for a liquid light guide medium that may be pumped through the lumen from a fluid source 314 coupled to the Y-connector 316 of the system 300. As the medium exits the distal end of the lumen 312 it travels through the pieces of shrink tubing and tubing segment 304, respectively, and out the distal tip 302.

A tail tube 318 may also be coupled to the Y-connector 310 to provide a conduit for liquid light guide medium and/or optical fiber between a source (not shown) and the Y-connector. When an optical fiber is provided, light energy from the light source travels through the fiber inside the tail tube 318 and Y-connector 316 to the open-ended catheter lumen 312. Alternatively, the tail tube 318 may transmit light energy using a liquid light guide medium in lieu of (or in addition to) an optical fiber. The distal end optical fiber may terminate before reaching the lumen 312, or inside the lumen 312. In both instances, the light energy originally traveling through the fiber may continue through the liquid light guide medium in the lumen.

The optical fiber 309 may extend completely through the lumen 312 and second piece of shrink tubing 308, as shown. In this embodiment, the distal end of the optical fiber terminates inside the tubing segment 304, where the liquid light guide medium allows the light energy to travel to the distal end 302 before continuing through a fluid optical channel to the target matter. Additional embodiments may include having the optical fiber extend to the distal tip 302 or beyond the distal tip. The optical fiber may be made from and coated with a cladding material appropriate to transmit light at the wavelength of the light energy (e.g., about 308 nm) and may have a size about 300 μm to about 600 μm in diameter (e.g., 600 μm in diameter), or a bundle of fibers ranging from 50 μm to 130 μm core diameter in a quantity that fits within the lumen of the tubing. The bundle of small core-sized optical fibers can provide additional flexibility and tortuosity to maneuver around tight curves in a patient's vasculature.

The tubing segment 304 may be made from flexible, biocompatible materials with refractive indices that facilitate total internal reflection at the wavelengths of light energy used. As noted above, examples of materials that fulfill these criteria at the 308 nm wavelength include fluoropolymers (e.g., fluorinated ethylene propylene (FEP) or polytetrafluoroethylene (PTFE) material) with refractive indices below that of water, such as Teflon® AF2400™ and Teflon® FEP from DuPont. The pieces of shrink tubing 306, 308 may be made from, for example, polyamide polymers. In addition, the catheter lumen 312 may be made from a fluoropolymer, or some other material with the appropriate flexibility, biocompatibility and refractive index facilitating wall reflection to enable the transmission of the light energy through the liquid light guide medium.

Figure 4:
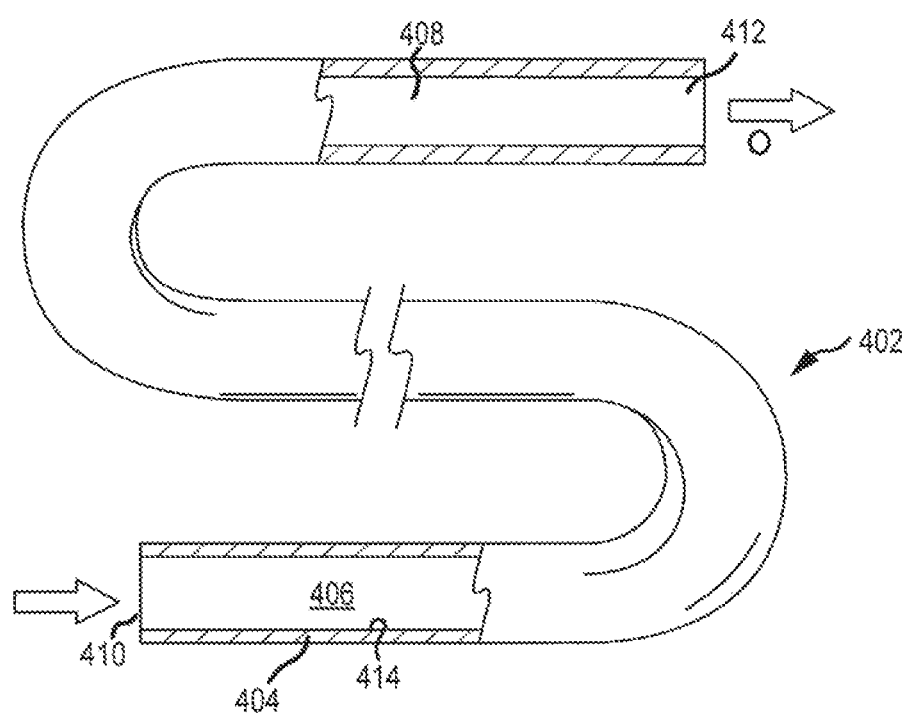
FIG. 4 shows a schematic of a catheter system that uses a liquid light guide medium to transmit light energy through the catheter lumen according to embodiments of the invention.

FIG. 4 shows an embodiment of a catheter lumen 402 that relies on a liquid light guide medium to transmit light energy. The catheter lumen 402 has a wall 404 that encloses the lumen 406. The lumen functions as a flow channel for liquid light guide medium 408 traveling from the proximal end 410 to distal end 412. Light energy travels through the medium by reflecting off the inner lumenal surface 414 at an angle conducive to total internal reflection. Still, some of the light energy is attenuated as it moves from the proximal end 410 (indicated by arrow "I") of the catheter lumen 402 out the distal end 412 (indicated by arrow "O"). The magnitude of the attenuation depends on the characteristics of the liquid light guide medium as well ax the characteristics of the tube wall and the number of the curves in the path of the lumen. The illustrated embodiment shows catheter lumen 402 having a circular cross-section, and may have transverse dimensions between about 0.5 mm to about 3 mm (e.g., about 0.7 mm to about 0.9 mm).

The materials used for wall 404 are selected in part based on the refractive index ($n_w$) of the wall of the inner lumenal surface 414. The refractive index $n_w$ should be less than the refractive index $n_f$ of the liquid light guide medium traveling through the lumen catheter 402. In other words, the ratio of the fluid refractive index ($n_f$) to the lumen wall refractive index ($n_w$) (i.e., $n_f/n_w$) is greater than 1.0. For example, the value of $n_f/n_w$ may be about 1.05 or more, about 1.1 or more, about 1.15 or more, etc.

The materials used for wall 404 are also selected in part to provide structural strength as well as flexibility so that the liquid-filled light guide may be bent through sharp curves without kinking or substantially distorting the cross-sectional geometry of the catheter lumen 402. These materials may include commercially available fluorinated ethylenepropylenes such as Teflon® FEP from DuPont, which has a relatively low refractive index of about 1.33, or Teflon-AF2400, which has an index of refraction of about 1.30.

Figure 5:
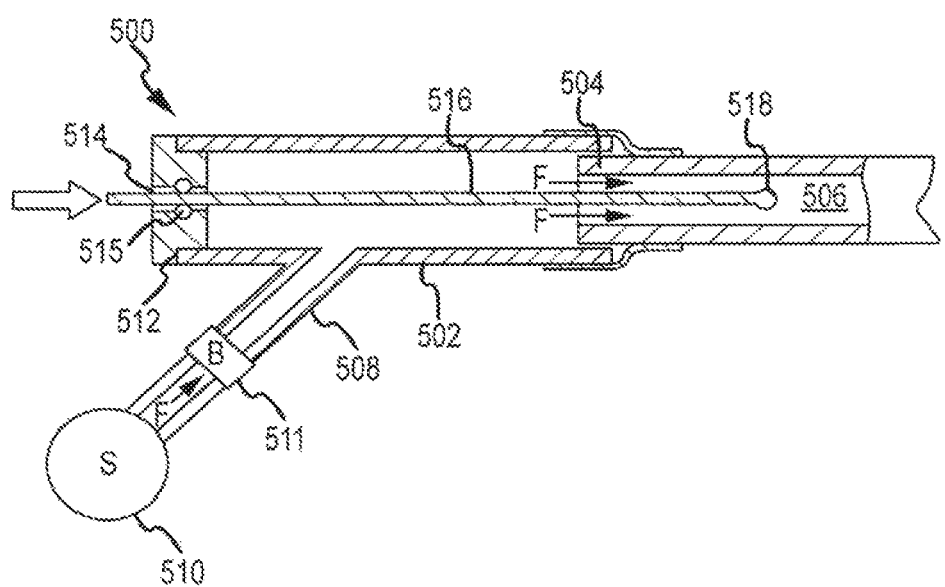
FIG. 5 shows a branched connector for a catheter system that contains an optical fiber according to embodiments of the invention.

FIG. 5 shows additional details of a branched Y-connector 500 for a catheter system according to embodiments of the invention. The Y-connector 500 includes a main barrel 502 whose distal end 504 is coupled to a catheter lumen 506. There is also a second branch 508 extending from the barrel 502 that establishes as fluid conduit between a liquid light guide medium source 504 and the Y-connector 500. The second branch 508 terminates at an inlet for liquid light guide medium to enter the Y-connector 500. The second branch may also include a bubble filter 511 between the source 504 and main barrel 502 that prevents bubbles in the medium from flowing into the barrel 502.

The proximal end 512 of the main barrel 502 has an inlet 514 for an optical fiber 516. The optical fiber 516 is used to transmit light energy into the catheter lumen 506 from a light source (not shown) optically coupled to the proximal end of the optical fiber 516. The inlet 514 may include an o-ring 515 that forms a fluid tight seal between the optical fiber 516 and barrel 502 to prevent liquid light guide medium from leaking out the proximal end 512, even when the optical fiber is being advanced or retracted in the Y-connector 500.

The distal end 518 of the optical fiber 516 is inserted through the proximal end 512 of the barrel to the catheter lumen 506. The fiber 516 may be advanced all the way to (or even through) the distal end of the lumen 506 (not shown), or may be advanced to a point behind the distal end of the lumen. When the optical fiber 516 is positioned proximal to the distal end of the lumen 506, light energy emitted from the tip of the fiber will travel through liquid light guide medium in the lumen 506 before exiting the catheter.

Exemplary Methods of Delivering Light Energy

Figure 6:
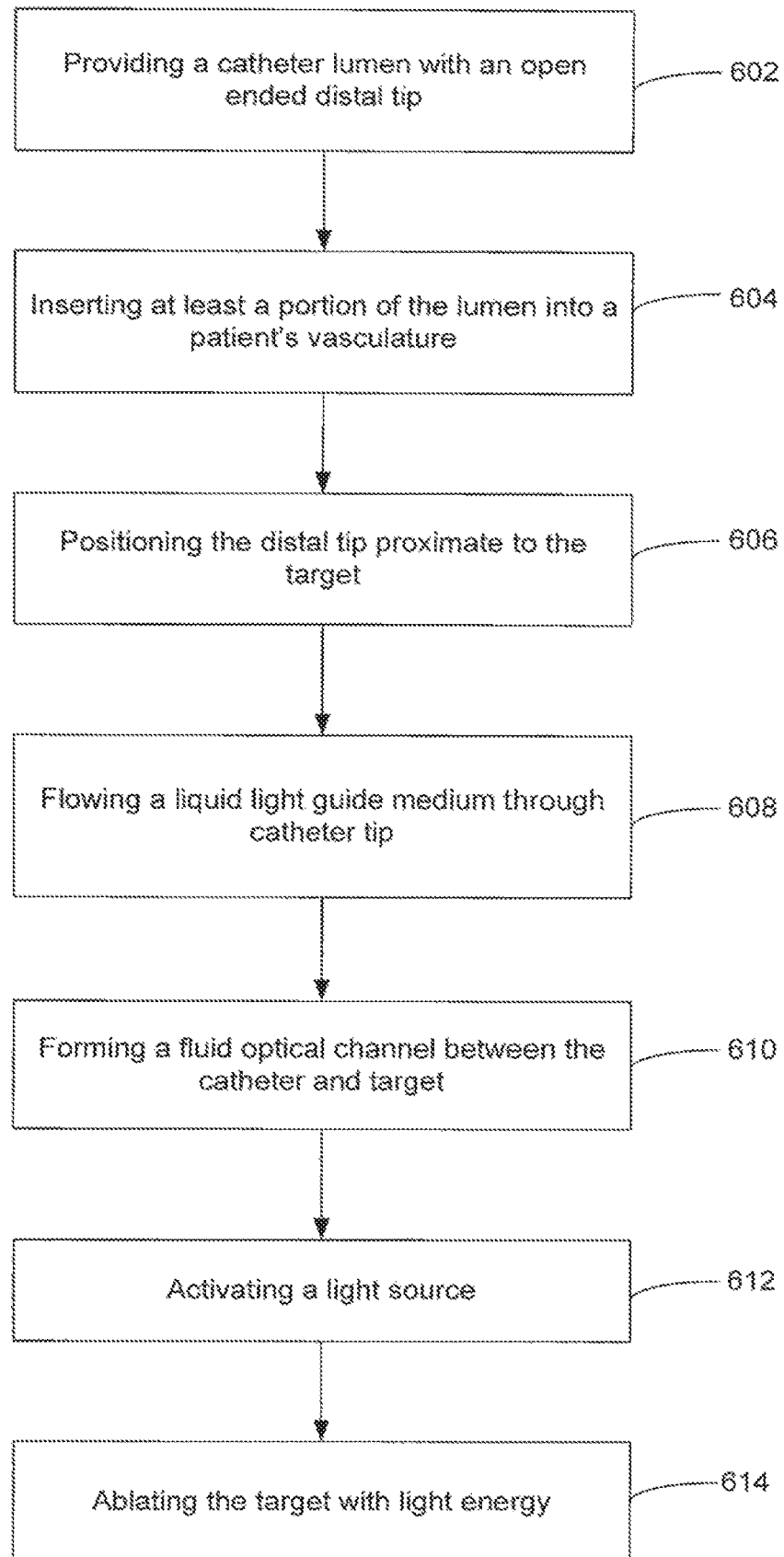
FIG. 6 is a flowchart illustrating selected steps in methods of delivering light energy to target matter according to embodiments of the invention.

FIG. 6 shows a flowchart illustrating selected steps in methods of delivering light energy to target matter according to embodiments of the invention. These steps may include providing a catheter lumen with an open-ended distal tip 602. The open-ended tip permits a liquid light guide medium to flow out of the catheter. At least a portion of the lumen, including the distal tip, is inserted into a patient's vasculature 604. The lumen may then traverse the vasculature until the distal tip is positioned proximate to target matter 606, such as a vascular occlusion. Embodiments include using a guidewire to help guide the lumen tip through the vasculature to the site of the target matter.

When the distal tip of the lumen is in position, a liquid light guide medium may flow through the catheter and tip 608. As the medium flows out of the catheter tip towards the target matter, it forms a fluid optical channel between the catheter and target 610. The core of this optical channel is the liquid light guide medium with its index of refraction. The patient's blood that surrounds the medium establishes a fluid optical cladding with a second index of refraction. A liquid light guide medium is selected so that the ratio of the index of refraction for the medium to the index of refraction for the surrounding blood is at least about 1.0, (e.g., least about 1.05, at least about 1.10, etc.).

The fluid optical channel provides a temporary optical path for light leaving the catheter to reach the target matter. Thus, the formation of the fluid optical channel is coordinated with activating a light source 612 that generates light energy for transmission through the catheter and fluid optical path to the target matter. As noted above, the light source may be a XeCl Excimer laser that generates a pulse of laser light at about 308 nm. The duration of the pulse may be shorter than the effective lifetime of the fluid optical channel.

When the light energy reaches the target material, it causes the ablation of the target material 614. In some embodiments, a single pulse of laser light energy may be sufficient to ablate the occlusion and reopen (or further open) a blood vessel. Alternatively, multiple cycles of fluid optical channel formation and light pulses may be performed to fully treat the target matter (e.g., fully open a blocked blood vessel).

EXPERIMENTAL

Figure 7A:
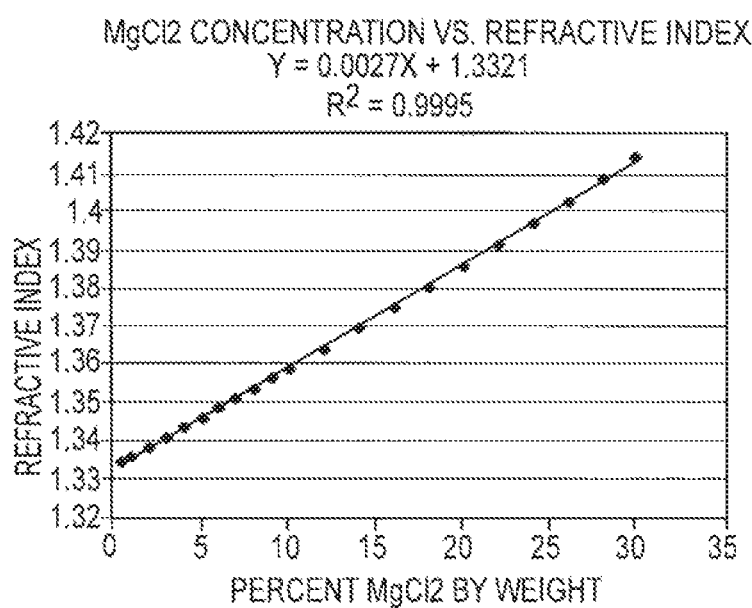
FIGS. 7A-C are plots of the refractive index versus concentration for solutions of magnesium chloride, calcium chloride, and sodium chloride.
Figure 7B:
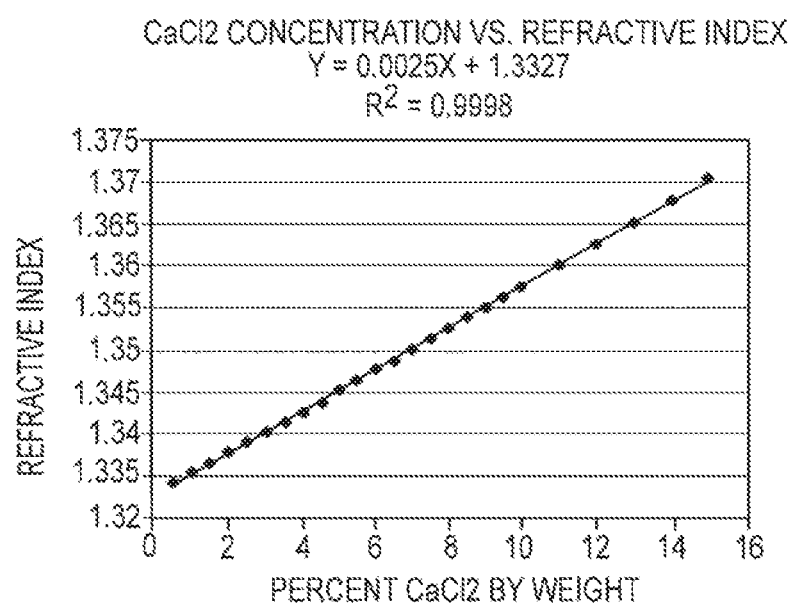
Figure 7C:
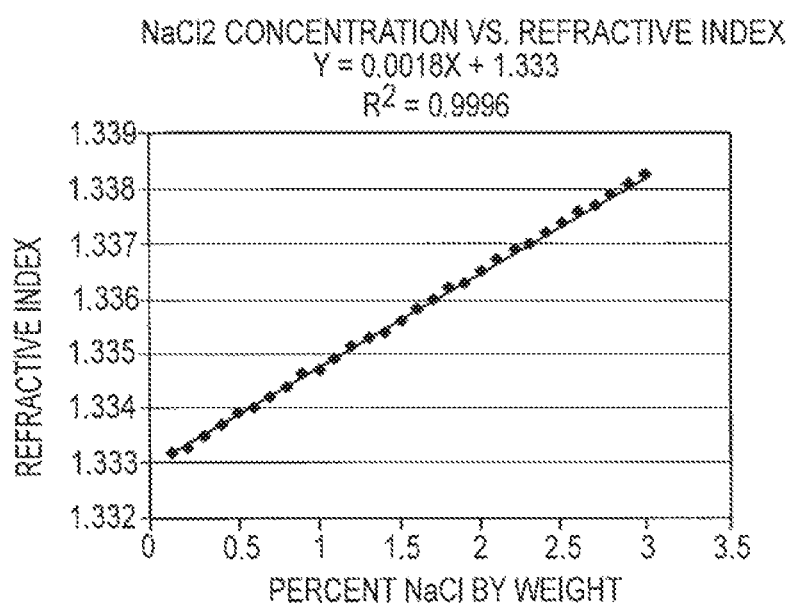

Indices of refraction for three aqueous salt solutions were measured as a function of the salt concentration in solution. The three salts were magnesium chloride hexahydrate ($MgCl_2.6H_2O$), calcium chloride ($CaCl_2$), and sodium chloride (NaCl). FIGS. 7A-C are plots of the refractive index versus salt concentration for the three solutions. FIG. 7A shows that increasing the concentration of a magnesium chloride hexahydrate solution from near 0% weight of the solution to 30% weight increases its index of refraction from about 1.335 to about 1.415. FIG. 7B shows that increasing the concentration of a calcium chloride solution from near 0% wt, to 15% wt. increases its index of refraction from about 1.335 to about 1.370. Finally, FIG. 7C shows that increasing the concentration of a sodium chloride solution from near 0% wt. to about 3% wt. increases its index of infraction from about 1.1332 to about 1.3385.

First derivates of the three lines plotted for FIGS. 7A-C indicate that the largest increase in the index of retraction per unit percentage increase in concentration occurred with the magnesium chloride hexahydrate solution (First Derivative=0.0027) compared with the calcium chloride solution (First Derivative=0.0025) and sodium chloride solution (First Derivative=0.0018). Because the refractive index of the magnesium chloride solution is more sensitive to changes in salt concentration, less concentrated solutions may be used to produce a high enough refractive index to cause total internal reflection between the liquid and the surrounding catheter lumen material or blood (i.e., the surrounding optical cladding material).

Additional experiments were run to record the absorption spectra of the three salt solutions at and around the wavelengths of light generated by a XeCl Excimer laser (i.e.,
around 308 nm. The absorption spectra were recorded for a wavelength range from 305 nm to 310 nm the absorption peaks for each of the aqueous ions (i.e., $Mg^{2+}$, $Na^+$, $Cl^-$) are listed in Table 1 below:

TABLE 1

Measured Absorption Peaks for Selected Aqueous Salt Ions from 305-310 nm

| Aqueous Ion | Measured Absorption Peaks (305-310 nm) | Number of Absorption Peaks |
|---|---|---|
| $Mg^{2+}$ | 307.423, 308.0208, 309.1065, 309.2984, 309.6890 | 5 |
| $Na^+$ | 305.3665, 305.5354, 305.6160, 305.7375, 305.8715, 306.4374, 306.6534, 307.0566, 307.0823, 307.832, 307.8747, 308.0251, 308.7057, 309.2731, 309.449, 309.5546 | 16 |
| $Ca^{2+}$ | 307.157, 307.695, 308.079, 309.930 | 4 |
| $Cl^-$ | 306.313, 307.136, 307.688 | 3 |

Table 1 indicates that sodium ions (Na+) have about 3 to 5 times the number of absorption peaks in the 305-310 nm wavelength range than magnesium, calcium or chloride ions. This correlates with the measurably higher absorbance rates for XeCl Excimer laser light that use a sodium chloride solution (an ingredient in standard buffered Saline solution) for a liquid light guide medium. The higher absorbance results in less of the light energy reaching the target matter (i.e., higher light attenuation).

Having described several embodiments, it will be recognized by those of skill in the art that various modifications, alternative constructions, and equivalents may be used without departing from the spirit of the invention. Additionally, a number of well known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these Smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the lumen" includes reference to one or more lumens and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A method of delivering light energy to target matter in a mammalian body, the method comprising:

inserting a portion of a catheter into a patient's vasculature, wherein the catheter comprises an open distal tip, a lumen extending proximally from the open distal tip and at least one optical fiber within the lumen;

positioning the open distal tip to be directed at the target matter;

providing a liquid light guide medium source fluidly coupled to the catheter lumen, wherein a bubble filter is arranged between the liquid light guide medium source and the catheter lumen, and wherein the liquid light guide medium source comprises a reservoir of a liquid light guide medium comprising magnesium chloride solution;

flowing the liquid light guide medium through the bubble filter to the open distal tip via a pump, wherein the liquid light guide medium flows to a distance extending farther than the distal end of the at least one optical fiber;

forming a fluid optical channel with the liquid light guide medium between the catheter and the target matter, wherein the liquid light guide medium comprises the magnesium chloride solution having an ion concentration that is isotonic with blood and tissue, wherein the magnesium chloride solution has a concentration of magnesium chloride up to 2.3% by weight, and wherein the magnesium chloride solution has an index of refraction that is greater than an index of refraction of the blood; and activating a laser light source to generate the light energy having a wavelength transmitted through the fluid optical channel to the target matter.

2. The method of claim 1, wherein the method further comprises ablating at least a portion of the target matter with the light energy.

3. The method of claim 1, wherein the magnesium chloride solution comprises at least one of an aqueous magnesium chloride solution, a pure magnesium chloride solution, solutions of anhydrous magnesium chloride, and solutions of hydrated magnesium chloride.

4. The method of claim 3, wherein the magnesium chloride solution comprises magnesium chloride hexahydrate (MgCl$_2$.6H$_2$O).

5. A method of ablating target matter in a mammalian body, the method comprising:

inserting a portion of a catheter into a patient's vasculature, wherein the catheter comprises an open distal tip, a lumen extending proximally from the open distal tip, and a wall enclosing the lumen, and at least one optical fiber within the lumen;

positioning the open distal tip to be directed at the target matter;

providing a liquid light guide medium source fluidly coupled to the catheter lumen, wherein a bubble filter is arranged between the liquid light guide medium source and the catheter lumen, and wherein the liquid light guide medium source comprises a reservoir of a liquid light guide medium comprising magnesium chloride solution;

flowing the liquid light guide medium through the bubble filter to the open distal tip via a pump, wherein the liquid light guide medium flows to a distance extending farther than the distal end of the at least one optical fiber;

forming a fluid optical channel with the liquid light guide medium between the catheter and the target matter, wherein the liquid light guide medium comprises the magnesium chloride solution having an ion concentration that is isotonic with blood and tissue, wherein the magnesium chloride solution has a concentration of magnesium chloride up to 2.3% by weight, and wherein the magnesium chloride solution has an index of refraction that is greater than an index of refraction of the blood;

activating a laser light source to generate the light energy having a wavelength transmitted through the fluid optical channel to the target matter; and ablating the target matter with the light energy.

6. The method of claim 5, wherein the magnesium chloride solution comprises at least one of aqueous magnesium chloride solutions, pure magnesium chloride solutions, solutions of anhydrous magnesium chloride, solutions of hydrated magnesium chloride, or combinations thereof.

7. The method of claim 6, wherein the magnesium chloride solution has an index of refraction between 1.335 and 1.420.

8. The method of claim 6, wherein the magnesium chloride solution comprises magnesium chloride hexahydrate (MgCl$_2$.6H$_2$O).

* * * * *